United States Patent [19]
Simada et al.

[11] Patent Number: 4,624,769
[45] Date of Patent: Nov. 25, 1986

[54] ELECTROPHORESIS APPARATUS FOR NUCLEIC ACID FRAGMENTS

[75] Inventors: Tamotu Simada, Akishima; Yoshinori Harada; Hideki Kambara, both of Hachioji; Keiichi Nagai, Tokyo; Jirou Tokita, Kokubunji, all of Japan

[73] Assignee: Hitachi, Ltd., Tokyo, Japan

[21] Appl. No.: 750,778

[22] Filed: Jul. 1, 1985

[30] Foreign Application Priority Data

Jun. 29, 1984 [JP] Japan .................................. 59-132876

[51] Int. Cl.⁴ ............................................ G01N 27/28
[52] U.S. Cl. .................................. 204/301; 204/182.8; 204/299 R
[58] Field of Search ................ 204/301, 299 R, 182.4, 204/182.5, 182.6, 182.8, 182.3

[56] References Cited

U.S. PATENT DOCUMENTS

| | | | |
|---|---|---|---|
| 3,720,593 | 3/1973 | Juhos | 204/299 R X |
| 3,844,925 | 10/1974 | Stathakos | 204/299 R |
| 3,932,265 | 1/1976 | Hoefer | 204/299 R |
| 4,479,861 | 10/1984 | Hediger | 204/299 R X |

*Primary Examiner*—John F. Niebling
*Assistant Examiner*—B. J. Boggs, Jr.
*Attorney, Agent, or Firm*—Antonelli, Terry & Wands

[57] ABSTRACT

An improved electrophoresis apparatus for nucleic acid fragments in which nucleic acid fragments are separated in the order of their molecular weight in an electrophoresis cell using an electrophoretic gel for determining the base sequence of a nucleic acid, the improvement comprising a nucleic acid fragment specimen supply section for supplying the nucleic acid fragments to the electrophoresis cell, disposed thereover a molecular sieving membrane having a predetermined degree of molecular permeability for separating to remove those high molecular weight ingredients in the nucleic acid fragment specimen other than the fragments intended to be analyzed electrophoretically.

10 Claims, 4 Drawing Figures

ELECTROPHORESIS APPARATUS FOR NUCLEIC ACID FRAGMENTS

BACKGROUND OF THE INVENTION

This invention concerns an apparatus for determining the base sequence of a nucleic acid and, more specifically, it relates to a continuous electrophoresis detection system for nucleic acid fragments capable of determining the base sequence of a nucleic acid continuously at a high accuracy and higher speed.

The base sequence of a nucleic acid has heretofore been determined, for example, by Maxam-Gilbert's method (Methods in Engymology 65, pp. 495–701). In this method, a nucleic acid labelled with a radioisotope is chemically cut into fragments of the nucleic acid and then the fragments of different length are arranged in the order of their molecular weights in a gel support sandwiched between glass plates. Then, the gel support is detached from the glass plates for taking an autoradiogram therefor, by which the electrophoretic band containing radioactive fragments of the nucleic acid is detected to determine the base sequence of the nucleic acid. Explanation will be made for the conventional method of determining the base sequence of the nucleic acid fragments by the prior art referring to the drawing. FIG. 1 is a perspective view for the structure of a conventional electrophoresis apparatus for the nucleic acid fragments. As shown in the drawing, the electrophoresis apparatus comprises an electrophoretic gel 2 for nucleic acid fragments sandwiched between two sheets of glass plates 3, electrolyte cells 1 for immersing therein both ends of the electrophoretic gel 2 and a DC power source 10. In this apparatus, when a specimen of nucleic acid fragments labelled with a radioisotope, (for example $^{32}P$) is supplied to the slot 5 of the electrophoretic gel 2 and subjected to electrophoresis under a voltage Ev of about 50 V/cm per gel length, the nucleic acid fragments having an identical molecular weight move from the cathode to the anode while forming an electrophoretic band 4 respectively and move electrophoretically with a mobility substantially in an adverse proportion to the logarithm of their molecular weight. The base sequence of the nucleic acid is determined in the order of the molecular weights based on the electrophoretic pattern of the electrophoretic bands 4 of the nucleic acid fragments.

In the case of the Maxam-Gilbert's method, the nucleic acid fragments supplied to the slot 5 in FIG. 1 have a chain length of the bases in an average number of 1000 in view of the limitation from the restriction enzyme employed. The number of the bases for the nucleic acid fragments that can be analyzed in one electrophoretic process is from 400 to 500 and remaining nucleic acid fragments with longer chain length can not sufficiently be moved electrophoretically but remain near the slot 5 of the electrophoretic gel 2 shown in FIG. 1. In this case, although they can be caused to flow from the cathode end of the gel 2 by continuing the electrophoresis for a longer period of time, this is not practical since the separation of the electrophoretic band for the nucleic acid fragments becomes insufficient.

Furthermore, in the case of the Chain Terminator Sequencing Method (Methods in Engymology, 65, pp. 299–494), since the nucleic acid fragments for electrophoresis prepared upon determination of the nucleic acid base sequence are a mixture comprising ingredients with more than 7000 bases and ingredients with less than several hundreds bases, the components with more than 7000 bases are scarcely electrophoretized but remain near the slot 5 of the electrophoretic gel 2 also in this case. Accordingly, it has been difficult in either of the Maxam-Gilbert's Method and the Chain Terminator Sequencing Method to continuously supply various kinds of nucleic acid specimens and analyze the base sequence of the nucleic acids.

SUMMARY OF THE INVENTION

The object of this invention is to provide an electrophoresis apparatus, for determining the base sequence of an nucleic acid at a higher speed, capable of continuously analyzing a great amount of nucleic acid fragments with one and identical electrophoretic gel, by previously separating to remove those nucleic acid fragments, i.e., higher molecular weight ingredients other than the fragments intended to be separated electrophoretically and maintaining the ingredients of the electrophoretic gel constantly.

The feature of this invention for attaining the foregoing object resides in an improved apparatus for determining the base sequence of a nucleic acid by separating nucleic acid fragments in the order of their molecular weights in an electrophoresis cell using an electrophoretic gel, the improvement comprising a nucleic acid fragment specimen supplying portion for supplying nucleic acid fragments to an electrophoresis cell, disposed thereover a molecular sieving membrane (or membranes) having a predetermined degree of molecular permeability, whereby separating to remove those higher molecular weight ingredients in the nucleic acid fragment specimen other than those intended to be analyzed electrophoretically.

The molecular sieving membrane for use in this invention may be any of semi-permeable membranes (dialysis membrane, ultrafiltration membrane, etc.) or low concentration gel with a less gel content relative to the solution generally employed, provided that the membrane can separate to remove higher molecular weight ingredients of a specific length.

Referring more specifically to the molecular sieving membrane according to this invention, it may, for example, be a disc-like molecular sieving membrane which is divided into a plurality of sections each with a predetermined angle of center and adapted to be used continuously while replacing an used membrane section with a new one by rotating the disc by the predetermined angle of center, or cartridge type molecular sieving membrane of a trigonal, square or rectangular shape (although the configuration is not necessarily limited only thereto) having a replaceable structure.

Furthermore, this invention provides an electrophoresis apparatus for nucleic acid fragments of a structure, wherein an electroconductive solution cell is disposed between the nucleic acid fragment specimen supplying section and an electrophoresis cell and a urea supply cell is disposed below the electrophoresis cell, so that the ingredients for the electrophoretic gel is maintained constantly and the nucleic acid fragments can be analyzed electrophoretically for a long period of time continuously by a single and identical electrophoretic gel.

DETAILED DESCRIPTION OF THE PREFERRED EMBODIMENT

Figure 1:
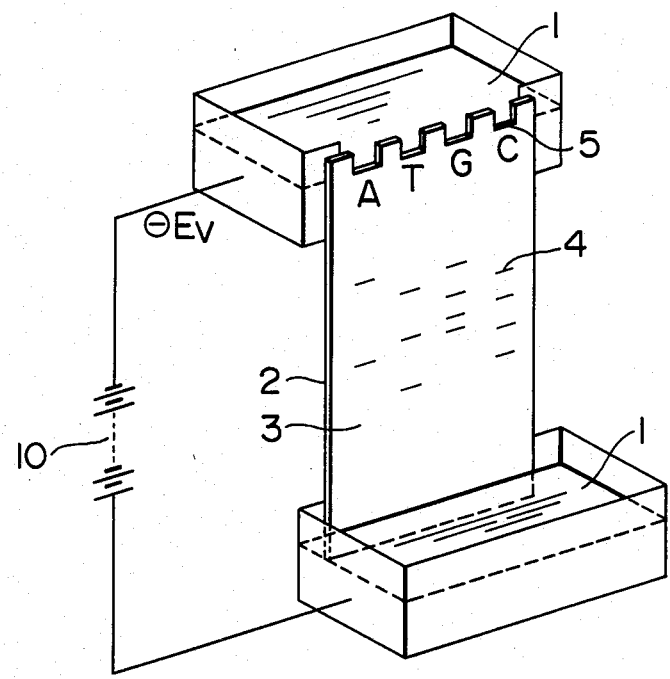
FIG. 1 is a perspective view for the schematic structure of a conventional electrophoresis apparatus.

This invention will be described by way of its preferred embodiments referring to the drawings. In the drawings, those portions with identical functions carry the same reference numerals.

EXAMPLE 1

Figure 2:
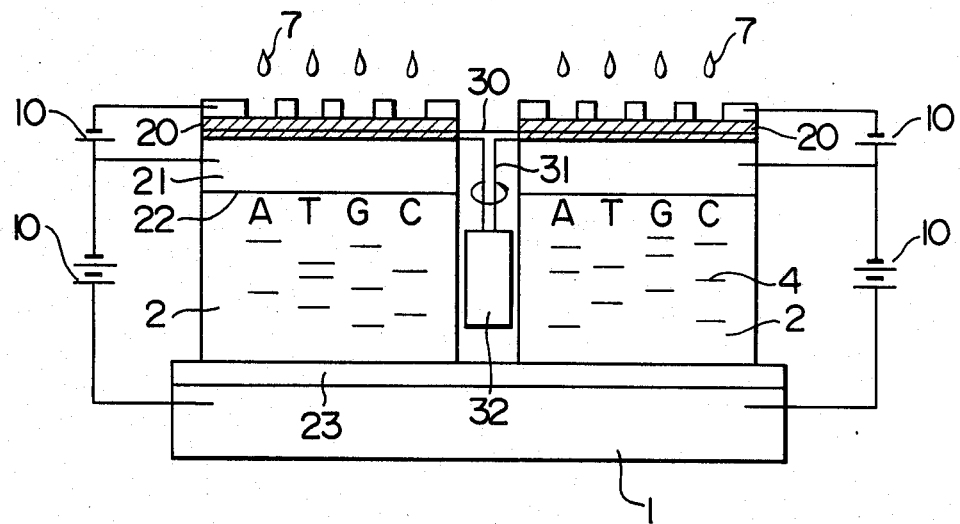
FIG. 2 is an explanatory view for the schematic structure of an electrophoresis apparatus using a disc-type molecular sieving membrane as one embodiment according to this invention.
Figure 3:
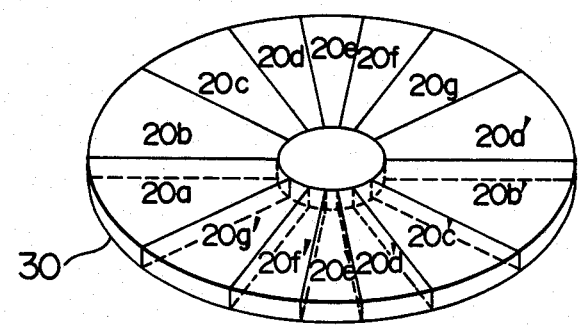
FIG. 3 is a perspective view showing the structure of the disc-type molecular sieving membrane.

FIG. 2 is an explanatory view for the schematic structure of an electrophoresis apparatus for nucleic acid fragments using a disc-type molecular sieving membrane as a preferred embodiment according to this invention. FIG. 3 is a perspective view for the structure of the disc-type molecular sieving membrane used in the electrophoresis apparatus according to this invention shown in FIG. 2. As can be seen from the drawings, nucleic acid fragments 7 for which the base sequence is to be determined are supplied to the electrophoresis apparatus. In this case, an electrophoresis cell 22 comprising a molecular sieving membrane 20 and an electroconductive solution cell 21 is disposed above an electrophoretic gel 2. Then, when a voltage is applied from a DC power source 10 to the electrophoresis cell 22, the nucleic acid fragments 7 start to move from above to downward in the electrophoresis cell 22. In this case, higher molecular weight components in the nucleic acid fragments 7 can not permeate the molecular sieving membrane 20 but remain thereon, while only the lower molecular weight ingredients in the nucleic acid fragments 7 permeate the electrophoresis cell 22 and reach the electrophoretic gel 2 for determining the base sequence of the nucleic acid. Since the nucleic acid fragments of the lower molecular weight ingredients intended to be determined for the base sequence of the nucleic acid form an electrophoretic band 4 by the conventional manner, the base sequence of the nucleic acid fragments 7 can be determined by analyzing the electrophoretic pattern in the electrophoretic band 4. The molecular sieving membrane 20 employed here has a structure of a disc-type molecular sieving membrane 30 as shown in FIG. 3, which is divided into a plurality of sections each with an appropriate angle of center. In one example of the disc-type molecular sieving membrane shown in FIG. 3, since the angle of center for dividing the molecular sieving membrane 20 is set to about 26 degree, fourteen molecular sieving membranes 20a–20g and 20a'–20g' can be formed on one sheet of the disc-type molecular sieving membrane 30. It is necessary that each of the molecular sieving membranes 20a–20g and 20s'–20g' divided into a narrow sector-like configuration has a sufficient size to cover the upper surface of the electrophoresis cell filled with the electrophoretic gel 2. As shown in FIG. 2, the disc-type molecular sieving membrane 30 is rotated, for example, each by about 26 degree interval on every predetermined of time by a motor 32 connected through a shaft 31 to the center of the membrane 30 so that the molecular sieving membranes 20a–20g and 20a'–20g' formed by dividing the disc-type molecular sieving membrane 30 is sequentially rotated for use. Further, as shown in FIG. 2, if the electrophoresis cells 22 each constituted with the electrophoretic gel 2 are disposed at two positions, two kinds of nucleic acid fragments 7 can be electrophoretically analyzed simultaneously, by which the entire analysis time can be shortened to one-half. In a case where the disc-type molecular sieving membrane 30 shown in FIG. 3 is used in this embodiment, the molecular sieving membranes 20a and 20a', for example, are used simultaneously for the first nucleic acid fragments to be subjected to electrophoresis to thereby determine the base sequence of the nucleic acids. Then, prior to the supply of new nucleic acid fragments to be analyzed electrophoretically next, the disc-type molecular sieving membrane 30 is rotated by about 26 degree, by which new molecular sieving membranes 20b and 20b' can be aligned with the upper surface of the electrophoretic gel 2 and the electrophoretic analysis for the nucleic acid fragments can be performed successively. In this way, the base sequence of the nucleic acids can be determined continuously for seven times in this embodiment.

By the way, when the electrophoresis for the nucleic acid fragments is continued under the foregoing conditions, since urea contained in the electrophoretic gel 2 moves electrophoretically, although little by little, from the anode to the cathode, the urea concentration is gradually reduced from the anode end of the electrophoretic gel 2. As the result, since no sufficient modifying condition can be maintained for the nucleic acid fragments within the gel, abnormality occurs in the electrophoretic state of the electrophoretic band 4 to make the result of the electrophoretic analysis inaccurate. In view of the above, according to this invention, a urea supply cell 23 containing a solution of the same composition as that of the solution ingredients in the electrophoretic gel 2 is disposed between the electrophoretic gel 2 and the electrolyte cell 1 on the anode side as shown in FIG. 2, so that urea may be supplied during electrophoresis to maintain the urea concentration always constant in the electrophoretic gel 2.

As described above, according to this invention, higher molecular weight ingredients in the nucleic acid fragments are eliminated and the modifying conditions for the nucleic acid fragments in the electrophoretic gel is always maintained constantly, whereby the electrophoretic gel can be prevented from being degraded and the gel can be re-used. Thus, a plurality kinds of nucleic acid fragments can be processed continuously and the analyzing speed can be significantly improved as compared with that in the conventional electrophoretic analysis method.

EXAMPLE 2

Figure 4:
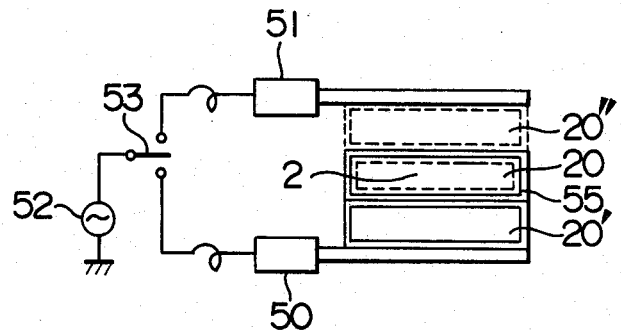
FIG. 4 is a plan view of an electrophoresis apparatus using a cartridge type molecular sieving membrane as one embodiment according to this invention.

Another embodiment according to this invention will now be described referring to FIG. 4. FIG. 4 is a plan view of an electrophoresis apparatus in this modified embodiment as viewed from above. The molecular sieving membrane 20 used in this embodiment is a cartridge-type rectangular molecular sieving membrane which is set in a molecular sieving membrane vessel 55 whose peripheral part is made of magnetizable material and which is disposed in such a configuration to completely cover the upper surface of the electrophoresis cell filled with an electrphoretic gel 2. Adjacent to the molecular sieving membrane vessel 55 is disposed a new molecular sieving membrane 20' for replacement while being contained in the vessel made of magnetizable material and attracted to secure on the side of a magnetic solenoid 50. Upon start of the electrophoresis for new nucleic acid fragments, a voltage is supplied from an AC power source 52 to a magnetic solenoid 51 by turning a switch 53. Then, the magnetizable vessel containing the molecular sieving membrane 20 and a new molecular sieving membrane 20' for replacement is attracted to secure on the side of the magnetic solenoid 51, and the used molecular sieving membrane 20 is detached from the upper surface of the electrophoresis cell for the electrophoretic gel 2 and the magnetizable vessel containing the new molecular sieving membrane 20' moves to completely cover the upper surface of the electrophoresis cell for the gel 2, to enable electrophoretic analysis successively. Next, another new molecular sieving membrane 20' is previously prepared and moved through attraction to the side of the magnetic solenoid 50 by energizing the solenoid 50. Then, the used molecular sieving membrane 20' is detached and the new molecular sieving membrane 20" is disposed above the electrophoresis cell for the electrophoretic gel 2. By repeating the foregoing procedures, a plurality of kinds of nucleic acid fragments can be analyzed continuously at a high speed.

Additional explanation will now be made for the parts and materials constituting the electrophoresis apparatus according to this invention.

Referring at first to the molecular sieving membrane 20 used in this invention, since the membrane is used for permeating only the lower molecular weight ingredients in the nucleic acid fragments, which are the specimen to be analyzed electrophoretically, it may be composed of a known semi-permeable membrane having a pore size capable of permeating therethrough those nucleic acid fragments of less than 500 bases, or of less than 200,000 molecular weight and thus permeating molecules selectively. The material for the membrane may comprise, for example, cellulose acetate, polyacrylonitrile, polysulfone, aromatic nylon, high molecular electrolyte composite compound, polyfluorovinylydene, Cuprophan ® membrane and the like, as well as synthesized zeolite (molecular sieves), silica gel and alumina gel. Furthermore, it is of course possible to achieve an equivalent effect by using a low concentration agarose gel or acrylamide gel with a less gel content relative to the solution (colloidal solution solidified into a jelly state).

Then, referring to the electrophoretic gel 2 used in this invention, an acrylamide gel with a large gel content relative to the solution and containing urea at a high concentration is suitable for example.

Further, it is necessary that the solution ingredient in the electroconductive solution cell 21 has the same solution ingredient as that in the electrophoretic gel 2 in order to maintain the modifying conditions for the nucleic acid fragments. Furthermore, the ingredients of the solution in the electrolyte cell 1 corresponds to the solution ingredients in the electrophoretic gel 2 except for the elimination of urea.

Further, the motor 32 for rotating the disc-type molecular sieving membrane 30 of the electrophoresis apparatus shown in FIG. 2 as a preferred embodiment according to this invention is required to rotate the disc-type molecular sieving membrane 30 at an optional angle and, accordingly, a step motor capable of obtaining an angle of rotation at a high accuracy corresponding to the number of input pulses is suitable.

As described above specifically, according to this invention, since the higher molecular weight ingredients of the nucleic acid fragments other than the fragments intended to be electrophoretically analyzed can be removed with ease and, further, the modifying conditions for the nucleic acid fragments in the electrophoretic gel can be always kept at a constant condition by the supply of urea, specimens of a plurality of kinds of nucleic acid fragments can be analyzed electrophoretically while supplying them repetitively at predetermined time periods, and a great amount of deoxyribonucleic acid (DNA) fragments can be analyzed by one and identical electrophoretic gel, thereby making it possible to automate the determination for the base sequence of the nucleic acids and obtain a high speed processing apparatus. Specifically, significant practical advantages can be obtained, for example, as described below:

(1) Preparation for the electrophoretic gel which has been carried out on every electrophoretic analysis for each specimen of the nucleic acid fragments is no more necessary and the time for the procedures can be shortened by about three hours per one analytical process.

(2) Furthermore, since the nucleic acid fragments of higher molecular weight ingredients, which remained in the electrophoretic gel in the prior method, can easily be removed according to this invention, a great amount of nucleic acids can be determined for their base sequence by automatic operation.

What is claimed is:

1. An improved electrophoresis apparatus for nucleic acid fragments in which nucleic acid fragments are separated in the order of their molecular weight in an electrophoresis cell using an electrophoretic gel for determining the base sequence of the nucleic acid, the supply of nucleic acid fragments including ingredients of higher molecular weight than the molecular weight of nucleic acid fragments to be separated in the electrophoresis cell, the improvement comprising a nucleic acid fragment specimen supply section for supplying nucleic acid fragments to said electrophoresis cell, disposed over a molecular sieving membrane having molecular permeability such that those higher molecular weight ingredients in the nucleic acid fragment specimen, other than the fragments intended to be analyzed electrophoretically, are removed, the nucleic acid fragment specimen supply section comprising at least one electrophoresis cell each having a milecular sieving membrane composed of a molecular sieving membrane, having a disc shape, divided into at least two sections each with a sector configuaration having a sufficient size to cover the upper surface of the electrophoresis cell, and a rotational mechanism disposed to the center of the molecular sieving membrane to constitute a structure capable of replacing the molecular sieving membrane by rotating the molecular sieving membrane each by an angle of center corresponding to the sector configuration at an arbitrary time interval.

2. An improved electrophoresis apparatus for nucleic acid fragments in which nucleic acid fragments are separated in the order of their molecular weight in an electrophoresis cell using an electrophoretic gel for determining the base sequence of the nucleic acid, the supply of nucleic acid fragments including ingredients of higher molecular weight than the molecular weight of nucleic acid fragments to be separated in the electrophoresis cell, the improvement comprising a nucleic acid fragment specimen supply section for supplying nucleic acid fragments to said electrophoresis cell, disposed over a molecular sieving membrane having a molecular permeability such that those higher molecular weight ingredients in the nucleic acid fragment specimen, other than the fragments intended to be analyzed electrophoretically, are removed, the nucleic acid fragment specimen supply section comprising at least one electrophoresis cell each having a molecular sieving membrane, of a cartridge shape, set in a casing, and a moving mechanism for moving the molecular sieving membrane by the extent of the space thereof so as to provide a structure capable of replacing the molecular sieving membrane by moving said molecular sieving membrane at arbitrary time intervals.

3. An improved electrophoresis apparatus for nucleic acid fragments as defined in claim 1 or 2, wherein the molecular sieving membrane disposed to the nucleic acid fragment specimen supply section is a semi-permeable membrane.

4. An improved electrophoresis apparatus for nucleic acid fragments as defined in claim 1 or 2, wherein the molecular sieving membrane disposed to the nucleic acid fragment specimen supply section is a low concentration gel.

5. An improved electrophoresis apparatus for nucleic acid fragments as defined in claim 1 or 2, wherein an electroconductive solution cell is disposed between the nucleic acid fragment specimen supply section and the electrophoretic layer.

6. An improved electrophoresis apparatus for nucleic acid fragments as defined in claim 1 or 2, wherein a urea supply cell is disposed adjacent to the electrophoresis cell.

7. An improved electrophoresis apparatus for nucleic acid fragments as defined in claim 6, further comprising an electrolyte cell adjacent the urea supply cell, on the side of the urea supply cell opposite the side thereof adjacent the electrophoresis cell.

8. An improved electrophoresis apparatus for nucleic acid fragments as defined in claim 1 or 2, wherein the membrane has a pore size capable of having nucleic acid fragments of less than 500 bases selectively permeate therethrough.

9. An improved electrophoresis apparatus for nucleic acid fragments as defined in claim 1 or 2, wherein the membrane has a pore size capable of having nucleic acid fragments of less than 200,000 molecular weight selectively permeate therethrough.

10. An improved electrophoresis apparatus for nucleic acid fragments as defined in claim 1 or 2, wherein the membrane is made of a material selected from the group consisting of cellulose acetate, polyacrylonitrile, polysulfone, aromatic nylon, polyfluorovinylidene, synthetic zeolite, silica gel and alumina gel.

* * * * *